United States Patent [19]

Cawley et al.

[11] Patent Number: 4,722,790

[45] Date of Patent: Feb. 2, 1988

[54] ON-LINE PLASMA MODIFICATION MEANS

[76] Inventors: Leo P. Cawley; Steven A. Bryant; Barbara J. Minard, all of 550 N. Hillside, Wichita, Kans. 67214

[21] Appl. No.: 727,924

[22] Filed: Apr. 29, 1985

Related U.S. Application Data

[63] Continuation-in-part of Ser. No. 417,704, Sep. 13, 1982, abandoned.

[51] Int. Cl.⁴ .............................................. B01D 27/02
[52] U.S. Cl. ..................................... 210/282; 210/506
[58] Field of Search ............... 210/679, 782, 282, 483, 210/504, 506, 927, 484

[56] References Cited

U.S. PATENT DOCUMENTS 4,103,685 8/1978 Lupien et al. ........................ 210/927
4,111,813 9/1978 Preus .................................... 210/484

Primary Examiner—Ivars Cintins
Attorney, Agent, or Firm—John Wade Carpenter

[57] ABSTRACT

A pliable compressible, liquid impervious bag having at least one integral part with a bag hole extending entirely therethrough. The bag includes a structure defining a bag aperture for communicating with the inside of the bag. A plurality of beads is positioned in the bag, and the beads are covalently coupled with a binder. A method for liquid modification comprising installing into a centrifuge bowl the pliable liquid impervious bag having the plurality of beads. A centrifuge cover is secured to the centrifuge bowl, and a liquid having matter to be removed is introduced into the pliable bag. The centrifuge bowl is spun at a predetermined speed in order to mix vigorously the liquid with the beads in the bag in order to expose the beads to a matter within the liquid such that the exposure enables the matter to attach and adsorb to the exterior surface of the beads. The method additionally comprises separating the stripped liquid phase from the pliable bag and the beads including the adsorbed matter that has been removed from the liquid.

6 Claims, 18 Drawing Figures

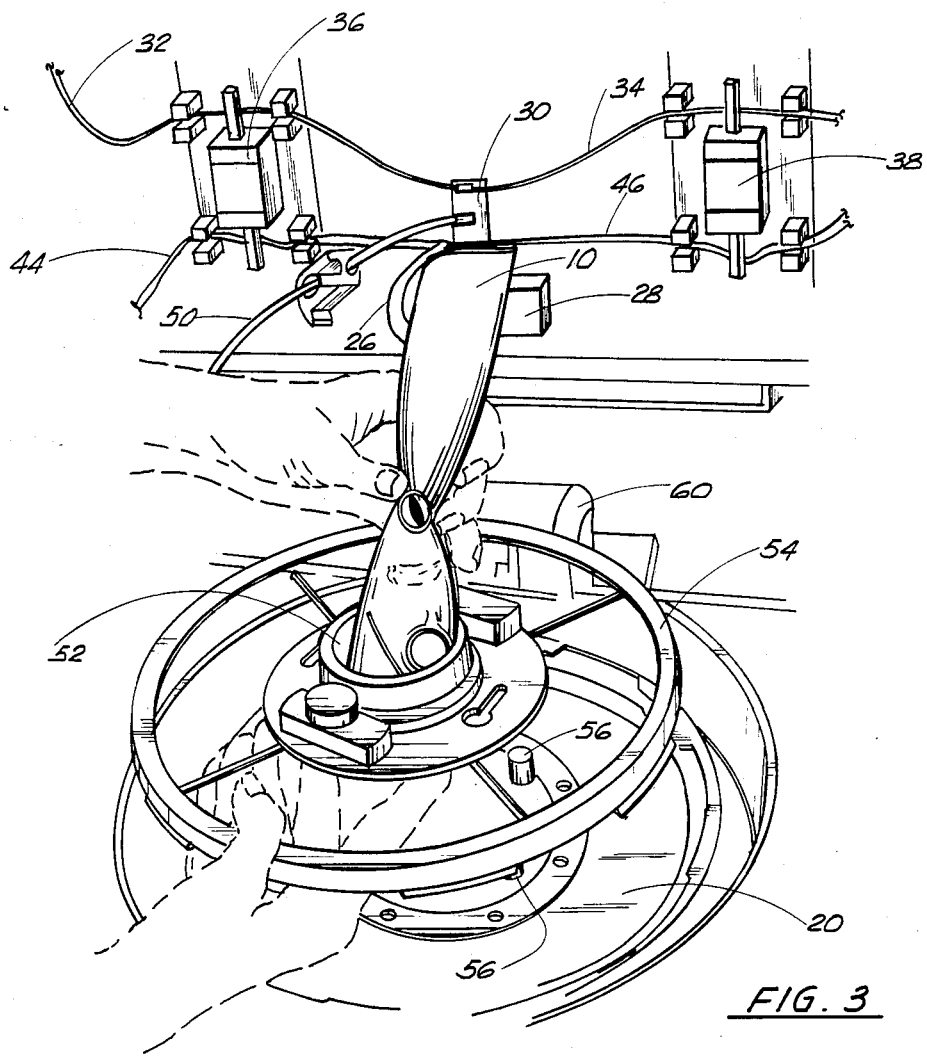
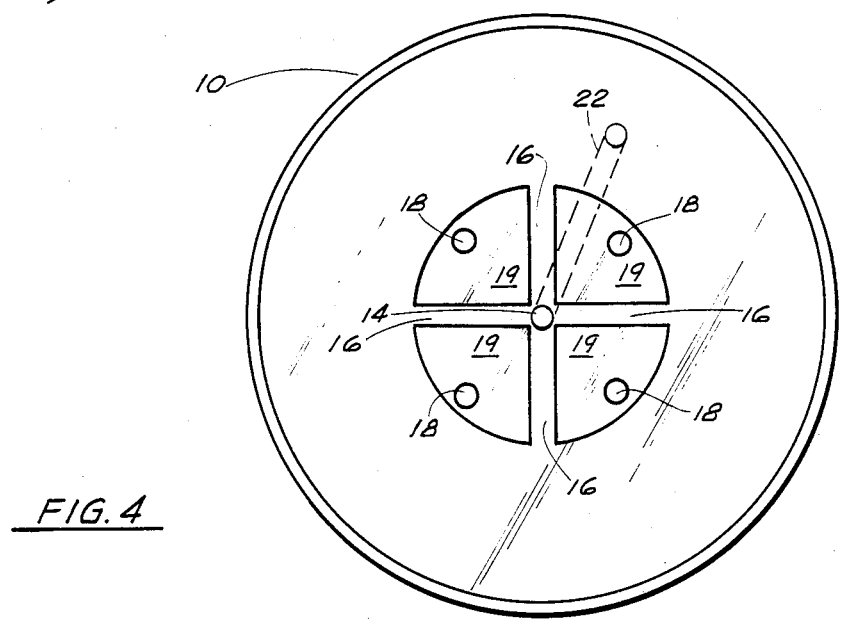

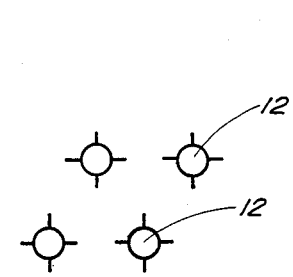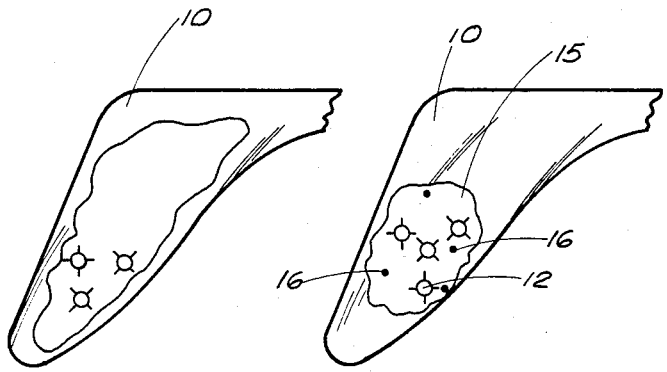
FIG. 9    FIG. 10    FIG. 11
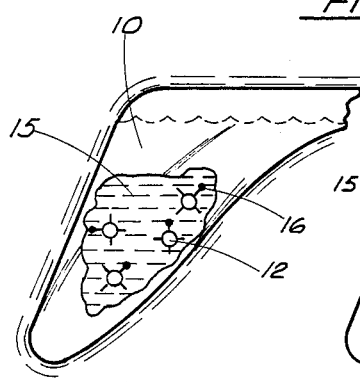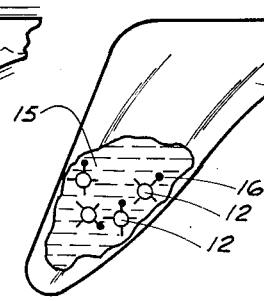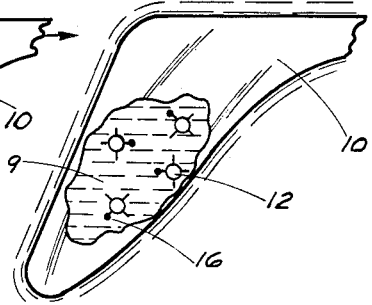
FIG. 12    FIG. 13    FIG. 14
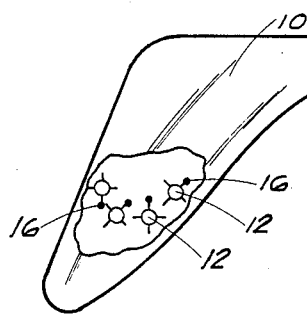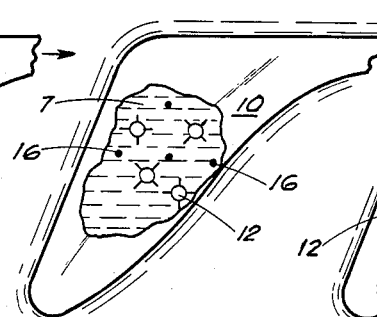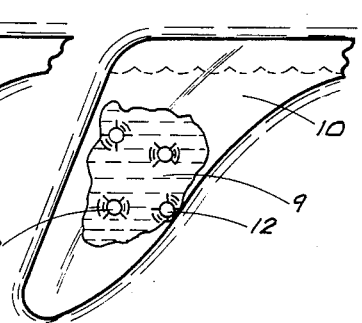
FIG. 15    FIG. 16    FIG. 18
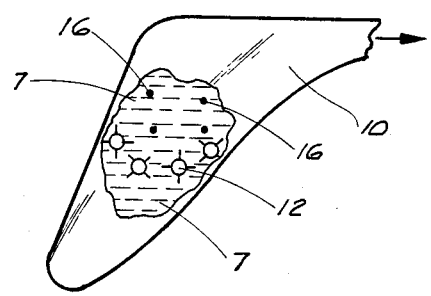
FIG. 17

ON-LINE PLASMA MODIFICATION MEANS

BACKGROUND OF THE INVENTION

This is a continuation-in-part patent application of our co-pending patent application filed on Sept. 13, 1982 and having Ser. No. 417,704, now abandoned.

1. Field of the Invention

This invention is related to beads in a bag. More specifically, this invention provides for a batch method employing coated beads in a pliable compartment for isolation and purification of all types of molecules, cells or organisms by solid phase affinity.

2. Description of the Prior Art

U.S. Pat. No. 4,143,201 by Miyashiro et al teaches a matrix comprising a water-insoluble beta-1, 3-glucan gel in the shape of beads. U.S. Pat. No. 3,522,172 by Pretories et al discloses a chromatographic process and apparatus. U.S. Pat. No. 3,981,801 by Knox illustrates a gradient storage method for liquid chromatography. U.S. Pat. No. 3,224,586 by Wade teaches a bag assemblage useable for removing impurities from a given quantity of liquid. U.S. Pat. No. 3,223,619 to Calmon et al provides for a radioactive fallout treatment kit. U.S. Pat. No. 4,103,685 to Lupien et al teaches a blood transfusion bag containing therein a divalent metallic complex of sulfated polysaccharide coupled to an activated non-sulfated polysaccharide gel. Terman et al in U.S. Pat. No. 4,215,688 discloses an apparatus for the extra corporeal treatment of disease in which a specific immunological reactant is removed from plasma which has been separated from whole blood. Neither Lupien's bag or Terman's are capable of being centrifuged. None of the foregoing prior art teach or suggest the particular bag and beads, plus method, of this invention.

SUMMARY OF THE INVENTION

The present invention accomplishes its desired objects by broadly providing a means for isolation and purification of all types of molecules, cells, or organisms, or the like, comprising a pliable compressible, liquid impervious bag means. The bag means has at least one integral part with a bag hole extending entirely therethrough, and a structure defining a bag aperture for communicating with the inside of the bag means. A plurality of bead means is positioned in the bag means. The bead means are coated with a binder covalently coupled thereto. The present invention also accomplishes its desired objects by broadly providing a method for liquid modification comprising the steps of installing into a centrifuge bowl means a pliable liquid impervious bag means having a plurality of bead means covalently coupled by a binder means, and securing a centrifuge cover means to the centrifuge bowl means. A liquid having matter to be removed is introduced into the pliable bag means, and the centrifuge bowl means is spun at a predetermined speed in order to mix vigorously the liquid with the bead means in the bag means in order to expose the bead means to the matter within the liquid such that the exposure enables the matter to attach and adsorb to the exterior surface of the bead means. The method finally comprises the steps of separating the stripped liquid phase from the pliable bag means and the bead means including the adsorbed matter that has been removed from the liquid.

Therefore, it it an object of the present invention to provide a means for on-line plasma modification and method for the same.

It is another object of this invention to provide an automated batch procedure for liquid modification including isolation and purification of all types of molecules, cells, or organisms, or the like.

These toegether with various ancillary objects and features will become apparent to those skilled in the art as the following description proceeds, are attained by this method and pliable bag having the beads, a preferred embodiment being shown with reference to the accompanying drawings, by way of example, only, wherein:

BRIEF DESCRIPTION OF THE DRAWINGS

FIG. 3 is a perspective view of the pliable bag containing the beads being rolled-up for passing through the center hole of a centrifuged cover;

FIG. 4 is a top plan view of the preferred embodiment of the pliable bag:

FIG. 9 is a perspective view of coated beads:

FIG. 10 is a partial sectional view of the beads positioned in the bag in a centrifuge bowl;

FIG. 11 is a partial sectional view of the beads and the liquid having matter to be stripped positioned in the bag;

FIG. 12 is a partial sectional view of the bag of FIG. 11 being agitated so that the matter to be stripped attaches to the beads;

FIG. 13 is a partial sectional view of the bag of FIG. 12 with the liquid phase stripped of the matter;

FIG. 14 is a partial sectional view illustrating the wash-mix being added to the bag of FIG. 13 after the stripped liquid phase is removed;

FIG. 15 is a partial sectional view disclosing the wash fluid being discarded;

FIG. 16 is a partial sectional view depicting the elution fluid being admixed vigorously with the beads having stripped matter attached thereto in order to remove the matter from the beads:

FIG. 17 is a partial sectional view disclosing isolation of the stripped matter in the eluate; and FIG. 18 is a partial sectional view disclosing the bag containing the beads with a wash-mix after removal of the eluate of FIG. 17 including the stripped matter.

DEATILED DESCRIPTION OF THE INVENTION

Figure 1:
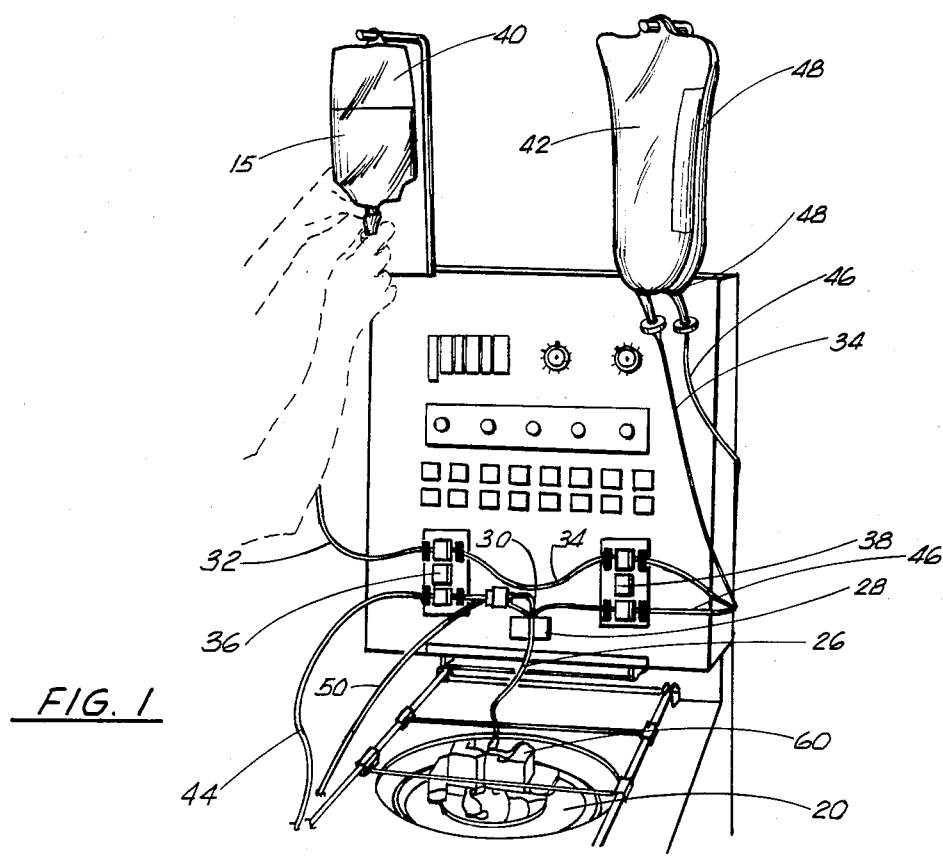
FIG. 1 is a perspective view of the pliable bag containing the beads mounted into a centrifuge bowl of a centrifuging machine with a spike being inserted into a plasma container for feeding the plasma into the pliable bag.

Referring in detail now to the drawings, wherein like or similar parts of the invention are identified by like reference numerals, and particularly initially in FIGS. 4 and 9–18, there is seen a pliable compressible, liquid impervious compartment or bag, generally illustrated as 10, containing a plurality of beads 12. The bag 10 or compartment may be made of any pliable, compressible, flexible, liquid impervious material, transparent or otherwise, and may be of any size or shape as long as it is capable of being subjected to centrifuging in a centrifuge machine. In a preferred embodiment of the invention the bag 10 is made of polyethylene, the clear type, and is shaped like a thin double walled pancake or a donut.

Figure 2:
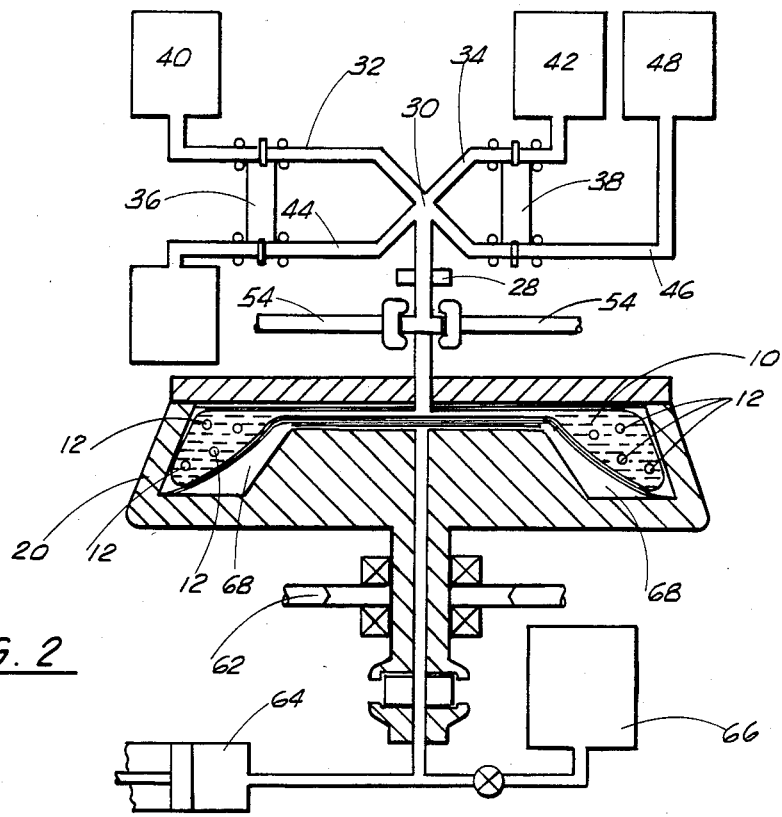
FIG. 2 is a schematic view of the liquid modification process.

In a more preferred embodiment of the bag 10 as illustrated in FIG. 4, bag 10 is circular double walled and shaped as a pancake with a bag aperture 14 centrally disposed with respect thereto in order to communicate with the inside of the bag 10. Four double walled fluid paths 18 are radially positioned from the bag aperture 14 in order to transport fluids from and to the peripheral sections of the bag 10. The borders of the fluid paths 16 are defined by four integral, single (or secured double) walled parts 19, with each part 19 having a bag hole 18 extending entirely therethrough. No fluids are capable of entering the integral parts 19 as the parts 19 are sealed off from the rest of the bag 10. This preferred embodiment of the bag 10 is ideal for centrifuging as the integral parts 19 with their respective bag holes 18 offer a means for retaining the bag 10 in a centrifuge bowl 20 (see FIGS. 1, 2 and 3) which readily distinguishes the bag 10 over the bag of Lupien et al in U.S. Pat. No. 4,103,685 which cannot be subjected to centrifuge, and which cannot be continuously operated in an on-line procedure as the bag 10 of this invention.

The beads 12 are preferably made from any suitable inert solid material such as glass, latex, polyacrylamide, polygluteraldehyde, polysaccharides, polymethylmethacrylate, cellulose, dextran, starch and agarose, as well as their derivatives, and can be constructed to contain magnetic particles for better separation. The diameter of the beads 12 can vary from 5 to 1000 u, and can be used in this invention as carrier materials for immobilized enzymes, to exchange, specific proteins, lipids, antigens, (e.g. fibronectin), antibody, toxins, cells, bacteria, viruses, organisms, on-line harvesting of products from tissue cultures (monoclonal antibodies, antisera), automation of extracorporeal immunoadsorption (removal of immune complexes, removal of antigen or antibody), isolation of immune complexes for further investigation (specifically identification of the antigen), removal and isolation of specific components of cells by extracorporeal immunoadsorption, continuous on-line cell culturing (monolayers, suspension, bacterial), recombinant DNA culturing, destruction of offensive components by solid phase enzymes, and other application. In a preferred embodiment of the invention, the beads 12 are covalently coupled (see FIG. 9) for isolation and recovery of specific proteins, antigens, antibody, cells, bacteria, viruses and other organisms; and especially for purification of plasma of immune complexes in extracorporeal immunoadsorption. Covalently coupling of the beads 12 as a carrier material for isolation and recovery of any of the foregoing matter can be carried out by a number of any well known procedures, and the covalently coupled beads 12 should specifically adsorb and should not adsorb nonspecifically.

In a preferred embodiment of the invention, the beads 12 coated with the binder (antibody, antigen, cells or organisms) are placed in the bag 10 through a bag conduit 22 (see FIGS. 4, 5 and 6) that is secured to the bag aperture 14. The beads 12 enter the periphery sections of the bag 10 through one of the four fluid paths 18. Preferably, the bag 10 containing beads 12 coated with the binder (antibody, antigen, cells or organisms) is used as a solid phase in an automated on-line batch method of affinity adsorption.

Figure 5:
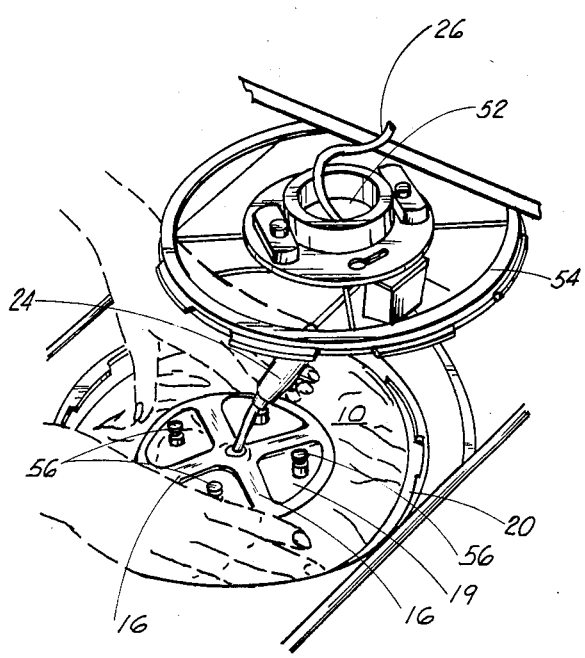
FIG. 5 is a perspective view of the pliable bag containing the beads being positioned into a centrifuge bowl.
Figure 7:
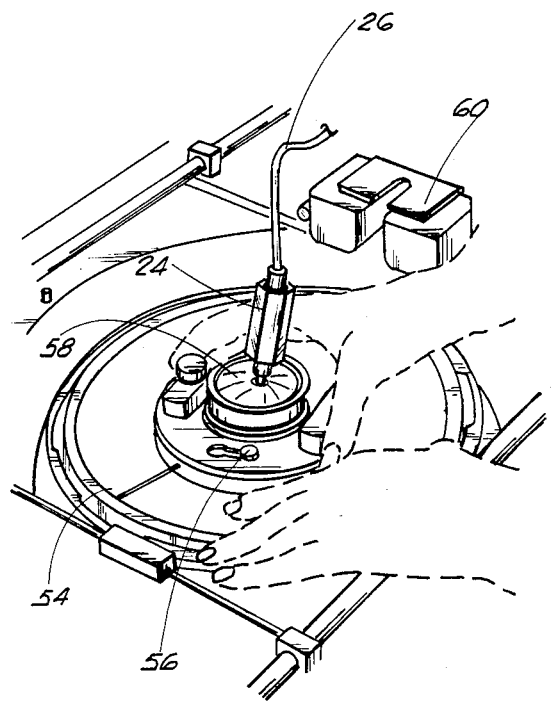
FIG. 7 is a perspective view of the centrifuge cover being installed over the pliable bag containing the beads.
Figure 6:
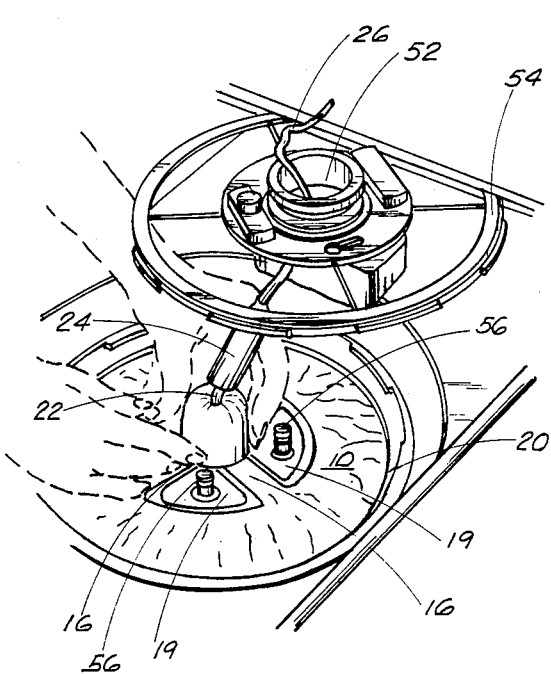
FIG. 6 is a perspective view of the pliable bag containing the beads having an alignment block positioned around the bag conduit.

The bag conduit 22 has a hexagonal seal 24 rotatably secured to the end thereof (see FIGS. 5, 6, and 7). Conduit 26 is secured to the other end of the hexagonal seal 24 and is passed through a bead detector assembly 28 to engage a junction manifold 30. Conduits 32 and 34 extend respectively from the junction manifold 30 through magnetic punching valves 36 and 38, respectively, to a liquid (e.g. plasma) container 40 and a wash solution container 42. Conduits 44 and 46 respectively attach from the junction manifold 30 through the valves 36 and 38, respectively, to a supernatant collect container 47 (see FIG. 2) and to a buffer fluid (or the like) container 48, respectively. Conduit 50 also extends to the supernatant collect container 47 from the junction manifold 30.

Figure 8:
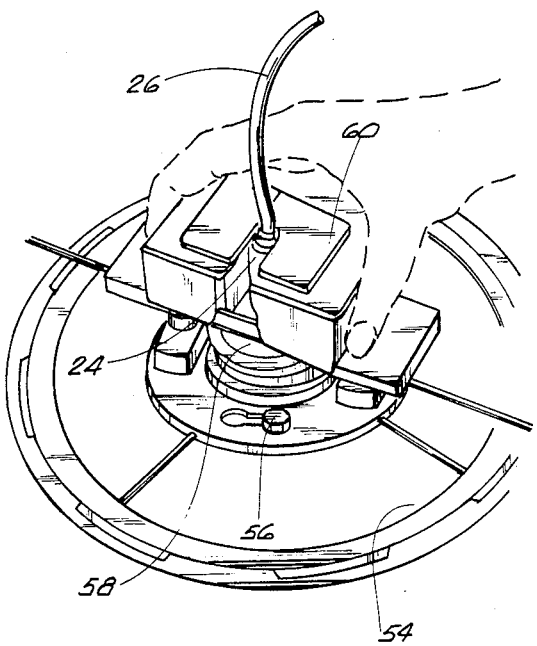
FIG. 8 is a perspective view of the seal weight being installed to rest on the centrifuge cover.

The automated on-line batch method of affinity adsorption is preferably conducted with an IBM 2991 Model 1 Blood Cell Processor TM or an IBM 2997 Blood Cell Separator TM. The bag 10 containing the beads 12 is rolled-up around the seal 24 and the bag conduit 22 (see FIG. 3) and is passed through a center hole 52 of a centrifuge cover 54 that rotatably connects to the centrifuge bowl 20 which includes studs 56 projecting vertically therefrom. The bag 10 with the beads 12 is installed in the centrifuge bowl 20 by positioning the four bag holes 18 over the four studs 56 on the centrifuge bowl 20. At least one alignment block 58 is positioned around the bag conduit 22 between the seal 24 and the bag 10. The centrifuge cover 54 is placed over the four studs 56 and rotated clockwise until the studs 56 engage the centrifuge cover 54 as illustrated in FIGS. 7 and 8. Securing of the centrifuge cover 54 to the centrifuge bowl 20 includes the positioning of the alignment block 58 into the center hole 52 of the centrifuge cover 54. The seal 24 is inserted into a seal weight 60, and the seal weight 60 is lowered until it rests against the top of the centrifuge cover 54 (see FIG. 8). The bag 10 containing beads 12 coated with the binder (antibody, antigen, cells or organisms) is now ready for an automated on-line centrifuge procedure to be used in a batch method of affinity adsorption.

A liquid 15 (e.g. plasma, etc.) included in the container 40 (see FIG. 1) contains matter 16 to be removed, and is introduced by gravity via conduit 32 into the bag 10 with the beads 12 (see FIG. 11) by opening valve 36 on conduit 32 to allow the liquid 15 to flow through conduit 32, through the junction manifold 30 and the bead detector 28, and through the conduit 26, the seal 24, and the bag conduit 22, and into the bag 10 which has been positioned in the centrifuge bowl 20. The centrifuge bowl 20 including the attached bag 10 is spun by a drive means 62 (see FIG. 2) at a predetermined speed in order to mix vigorously the liquid 15 with the beads 12 in the bag 10 in order to expose the beads 12 to the matter 16 within the liquid 15 such that the exposure sure enables the matter 16 to attach and adsorb to the exterior surface of the beads 12 (see FIG. 12). After affinity adsorption of the matter 16 by the beads 12, the stripped liquid phase 15 is subsequently expressed from the bag 10 (see FIG. 13) in order to separate the adsorbed beads 12 from the stripped liquid phase 15. The separation is accomplished by pumping with pump 64 (see FIG. 2) a membrane fluid from a fluid reservoir 66 into a membrane 68 in order to inflate the same, which forces the membrane against the bottom of the pliable bag 10 having the plurality of adsorbed beads 12 and stripped liquid 15 in order to push the stripped liquid phase 15 out of the bag 10. Membrane 68 expansion is conducted simultaneously with the spinning of the centrifuge bowl 20. Because the centrifugal force from the spinning bowl 20 generally keeps the beads 12 retained against the peripheral edges of the bag 10, there will be no bead 12 carryover into the stripped liquid phase 15 as it is being expressed from the bag 10, through the fluid paths 16 of the bag 10; through aperture 14, bag conduit 22, seal 24, and conduit 26; and through the bead detector 28 into the manifold 30 and out of the manifold 30 and into the supernatant container 47 via conduit 44. In the unlikely instance that there is carryover of any beads 12 with the stripped liquid phase 15, the beads 12 are detected by bead detector 28.

The stripped liquid phase 15 in container 47 may now be used for a variety of purposes such as where the matter 16 that was removed was an inhibitory substance of an undesirable component (e.g. plasma may be fed back to the patient after purification of plasma of immune complexes).

The beads 12 should preferably be regenerated for continuous use. Regeneration includes deflating membrane 68 and washing the adsorbed beads 12 with wash liquid 9 at least once (to remove any residual liquid phase 15), preferably at least twice. Wash liquid 9 contained in container 42 is introduced by gravity via conduit 34 into the bag 10 with the adsorbed beads 12 by opening valve 38 on conduit 34 to allow the liquid 9 to flow, simultaneously with the spinning of the bowl 20, through conduit 34, through the junction manifold 30 and the bead detector 28, and through the conduit 26, the seal 24, and the bag conduit 22 and into the bag 10 through its fluid paths 16 (see FIG. 14). The wash fluid 9 is expressed (see FIG. 15) from the bag 10 by inflating the membrane 68 while the centrifuge bowl 20 is spinning. The bead detector 28 can detect any carryover of the beads 12 with the wash fluid 9 which is to be discarded through conduits 44 or 50. An elution buffer fluid mix 7 is contained within container 48 and is admixed with the adsorbed beads 12 in order to release the bound matter 16 into the liquid elution fluid mix 7 (see FIG. 16). Admixture for regeneration of the beads 12 is accomplished through the gravity introduction of the buffer fluid mix 7 via conduit 46 into the bag 10 with the wash adsorbed beads 12. When the valve 38 on the conduit 46 is opened, the buffer fluid mix 7 is allowed to flow (simultaneously with the spinning of the bowl 20) through conduit 46, through the junction manifold 30 and the bead detector 28, and through the conduit 26, the seal 24, and the bag conduit 22 and into the bag 10 through its fluid paths 16. After the bounded matter 16 is released off of the beads 12 and into the liquid elution fluid mix 7, the eluate including the isolated matter 16 is harvested by separating, through the inflation of membrane 68 while the centrifuge bowl 20 is spinning, the deadsorbed beads 12 and the eluate (see FIG. 17). The bead detector 28 can detect any bead 12 carryover with the elution fluid mix 7. The harvested material is available for many desirable uses. The deadsorbed beads 12 are subsequently washed with wash fluid 9 (see FIG. 18) several times in order to remove eluating solution. This wash cycle is similar to the washing of the adsorbed beads 12, as previously described and illustrated in FIG. 14. At the completion of this washing cycle, the beads 12 are regenerated and can be recycled through the various process steps again for another liquid in container 40.

Thus, through the use of the IBM 2991 Model 1 Blood Cell Processor which is designed by IBM for washing human blood cells, we have discovered a system and a method to prepare affinity purified specific antibodies and to isolate and purify antigens through the utilization of the pliable bag 10 containing stable beads 12 covalently coupled to antigen or antibody. The bag 10 containing the beads 12 is both a container and a centrifuge head and replaces the present immunoadsorbent columns. It should be understood that while the preferred approach for utilization of the bag 10 containing the beads 12 is the automated approach of batch made affinity chromatography as has been described, the same procedure may be conducted with a nonautomated approach, such as manually performed.

As has been previously mentioned, a preferred use of our invention is for plasma immunoadsorption (extracorporeal immunoadsorption). Patients with autoimmune diseases, cancer, and infectious diseases have been shown to clinically benefit by plasma exchange. The explanation for the clinical benefit is believed to rest on the observation that these individuals have circulatory immune complexes, excess free antibody or antigen which interfere with the normal function of the immunologic system. Furthermore, these complexes or offensive agents are not effectively removed by the patient's clearance system. As the concentration of these immune complexes increase, they settle in vascular tissue of select organs, causing immune complex injury, which may lead to complete loss of organ function.

Plasma exchange (apheresis) has been used successfully in systemic lupus erythematosus (SLE), myasthenia gravis, idiopathic thrombocytopenia purpura, rheumatoid arthritis and malignancies. One major drawback of the procedure is the cost of the replacement components, the fresh frozen plasma and the normal human albumin.

Plasma immunoadsorption (extracorporeal immunoadsorption) differs from apheresis by attempting to remove from the blood only those agents that are responsible for the adverse affects of the disease; that is, the immune complexes. Plasma immunoadsorption has been referred to as "scrubbing the blood". Instead of exchanging the plasma, the plasma is selectively scrubbed (adsorbed) to remove the unwanted antigen-antibody complexes, antibodies, antigens or other offensive agents. The adsorbed plasma (scrubbed plasma) is reunited with cellular components and returned to the patient.

Our invention will be illustrated by the following set forth example which is given by way of illustration and not by any limitations.

EXAMPLE

Sephrose 4B beads 12 covalently linked with gelatin were placed in the bag 10 of FIG. 4. The bag 10 containing the sephrose 4B beads 12 was mounted in the centrifuge bowl 20. The beads 12, substituting for red cells, were permitted to come in contact with serum containing fibronectin. The isolate released by urea was shown by immunoelectrophoresis to contain fibronectin.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

We claim:

1. A means for isolation and purification and modification of a liquid comprising a pliable compressible, liquid impervious bag means, said bag means having at least one integral part with a bag hole therethrough that does not communicate with the inside of said bag means, and a structure defining a bag aperture for communicating with the inside of said bag means;

and a plurality of bead means positioned in said bag means, said bead means being made of an inert solid material and coated with a binder covalently coupled thereto, said binder is selected from the group consisting of antigen, antibody, toxins, cells, specific protein, bacteria, viruses, and mixtures thereof.

2. The means of claim 1 wherein said bag means is generally circular with said bag aperture generally centrally disposed with respect to said circular bag means;

and said circular bag means comprises four fluid paths radially disposed from said bag aperture in order to inject and remove fluids from the inside of said circular bag means, and four integral parts bordering on said four fluid paths, each of said integral parts includes a bag hole therethrough.

3. The means of claim 1 wherein said bead means is manufactured from a material selected from the group consisting of glass, latex, polyacrylamide, polygluteraldehyde, polysaccharides, polymethylmethacrylate, cellulose, dextran, starch and agarose, as well as their derivatives, and mixtures thereof, and comprise a diameter of from 5 to 1000 u.

4. The means of claim 1 wherein said bag means comprises four fluid paths radially disposed from said bag aperture in order to inject and remove fluids from the inside of said bag means.

5. The means of claim 4 wherein said bag means additionally comprises four integral parts bordering on said four fluid paths, and each of said integral parts includes a bag hole therethrough.

6. The means of claim 1 wherein said bag means comprises four integral parts with each integral part including a bag hole therethrough that does not communicate with the inside of said bag means.

* * * * *